(12) United States Patent
Leplianin

(10) Patent No.: US 8,865,792 B2
(45) Date of Patent: Oct. 21, 2014

(54) MEDICAL GLUE AND METHOD OF ITS PRODUCTION

(75) Inventor: Gennady Leplianin, Korolev (RU)

(73) Assignee: Elena Leplyanina, Korolev, Moscow region (RU)

( * ) Notice: Subject to any disclaimer, the term of this patent is extended or adjusted under 35 U.S.C. 154(b) by 0 days.

(21) Appl. No.: 14/237,938

(22) PCT Filed: Feb. 6, 2012

(86) PCT No.: PCT/RU2012/000066
§ 371 (c)(1),
(2), (4) Date: Feb. 10, 2014

(87) PCT Pub. No.: WO2013/022374
PCT Pub. Date: Feb. 14, 2013

(65) Prior Publication Data
US 2014/0213689 A1  Jul. 31, 2014

(30) Foreign Application Priority Data
Aug. 11, 2011  (RU) .................. 2011133552

(51) Int. Cl.
*A61L 24/06* (2006.01)
*A61L 24/00* (2006.01)
*C09J 141/00* (2006.01)
*C09J 4/00* (2006.01)

(52) U.S. Cl.
CPC ............... *A61L 24/06* (2013.01); *A61L 24/001* (2013.01); *C09J 141/00* (2013.01); *C09J 4/00* (2013.01)
USPC ........... 523/118; 606/213; 424/487; 528/362; 514/526

(58) Field of Classification Search
CPC .......... A61L 24/06; C07C 255/07; C09J 4/00; C09J 41/00
USPC ........... 523/118; 606/213; 424/487; 528/362; 514/526
See application file for complete search history.

(56) References Cited

U.S. PATENT DOCUMENTS

| 2005/0197421 A1* | 9/2005 | Loomis | ......................... 522/178 |
| 2010/0010536 A1* | 1/2010 | Baiker et al. | .................. 606/214 |

FOREIGN PATENT DOCUMENTS

| CN | 1418706 A | 5/2003 | |
| CN | 1850290 A | 10/2006 | |
| DE | 102005012473 A1 | 9/2006 | |
| SU | 1005455 A1 | 7/1991 | |
| WO | WO 9623532 A1 * | 8/1996 | ............. A61L 25/00 |

* cited by examiner

*Primary Examiner* — Michael Pepitone
(74) *Attorney, Agent, or Firm* — Nadya Reingand

(57) ABSTRACT

This invention relates to medicine, more specifically, to surgical devices, and can be used for gluing soft body tissues. The medical glue comprises 3-methacryloxysulpholane, N-butyl-2-cyanoacrylate and at least one stabilizer.

7 Claims, No Drawings

MEDICAL GLUE AND METHOD OF ITS PRODUCTION

CROSS-REFERENCE TO RELATED APPLICATIONS

This application is the U.S. national stage of International Application No. PCT/RU2012/000066, filed Feb. 6, 2012 and claims the benefit thereof, the entire contents of which is incorporated herein by reference.

This invention relates to medicine, more specifically, to surgical devices, and can be used for gluing soft body tissues.

Polymer glue compositions find wide application in various segments of medicine. Their use in surgery, therapy of burns, large wound surfaces and dermatological diseases, isolation of infection sites, sterilization of surgery areas etc. is often the most efficient method of achieving fast recovery which has well proven itself in clinical practice.

Stringent requirements are imposed on medical glues. The must glue tissues in wet environments at body temperature; rapidly form a strong and elastic adhesive film to securely hold the glued surfaces at all cicatrix formation stages; resolve during tissue regeneration; glue tissues without releasing toxic products or significantly increasing temperature; cause minimum local tissue response; have no carcinogenic or sensitizing action; be easily sterilizable or initially sterile; the adhesive film must not hinder tissue propagation through itself during their growth. Furthermore, glue composition components must not reduce the biological activity of medicines introduced therein but maintain their required concentration in the affected area for a relatively long time depending on situation.

Compositions based on $\alpha$-cyanoacrylic acid ethers have attracted special attention in the medical glue industry. The adhesive properties of cyanoacrylates were first reported in 1958, and their potential medical applications were reported in 1959.

Many cyanoacrylate medical glues produced by US, Japanese, German, Polish etc. companies are known.

Their disadvantages are too high solidification rate of the adhesive film on the tissue, high hardness and brittleness of the film, insufficient porosity and inflammatory response of tissues.

Cyanoacrylates gradually decompose in body providing resolution of the adhesive film. Most probably, polymer decomposition initiates with the hydrolysis of the complex ether group. This is followed by the detachment of the cyano group and the decomposition of the main macromolecular chain. If has been found that decomposition products are accumulated in the pituitary, brain, thyroid gland and liver. Decomposition rate depends on the size and type of the alkylic substituting group of cyanoacrylate. Some cyanoacrylates and their metabolites remain in body for up to 10 months.

To reduce the inflammatory response and increase the biocompatibility between body tissues and glue composition components, one can introduce anti-inflammatory and anti-microbial additions to the glue composition.

The vinyl bond of cyanoacrylates contains two electron acceptor groups: —C═O and —C≡N which determine their extremely high activity in anionic polymerization copolymerization reactions with vinyl monomers the vinyl bond of which contains electron donor substituting groups. When exposed to traces of moisture, alcohols, alkali or aminoacids, cyanoacrylates undergo polymerization by anionic mechanism (see diagram) to form high molecular weight linear polymers. The acrylate and the metacrylate groups readily polymerize by radical mechanism.

To stabilize those compositions, one should introduce at least two inhibitors; one to inhibit the anionic processes and the other to inhibit the radical polymerization.

Vinyl monomer polymerization is accompanied by massive heat release. The specific heat efficiency of methyl-$\alpha$-cyanoacrylate polymerization is 0.09 kcal/g. The formation rate of the adhesive film, i.e. the monomer polymerization rate on the covered (glued) surface should not exceed the threshold at which the polymerization heat cannot dissipate to the environment without significantly increasing body temperature. Overheating will cause tissue inflammation and necrosis.

High molecular weight $\alpha$-cyanoacrylates have lower specific heat efficiency of polymerization compared to methyl-$\alpha$-cyanoacrylate (the specific heat efficiency of butyl-$\alpha$-cyanoacrylate polymerization is 0.06 kcal/g), and their use in surgical adhesives is therefore preferred.

Known (SU Inventor's Certificate 1455709) is a glue composition used for gluing soft body tissues. The known composition comprises ethyl-$\alpha$-cyanoacrylate, butylacrylate and 3-methacrylcarboxysulpholene-2 (sulpholenemethacrylate, otherwise named methacryloxysulpholane). To produce the known composition, ethyl-$\alpha$-cyanoacrylate is mixed with butylacrylate and 3-methacrylcarboxysulpholene-2 in the required proportion and stir at room temperature until the complete dissolution of sulpholenemethacrylate.

Disadvantages of the known medical glue are insufficient storage stability and unpleasant odor.

Known (RU Patent 2156140) is a medical glue used in various segments of medicine. The known medical glue comprises the ethyl ether of 2-cyanoacrylic acid, butyl or hexyl ether of acrylic acid and 1,1-dioxotetrahydro-1$\lambda^6$-thiophene-3-ilic ether of 2-methacrylic acid.

To produce said glue one should mix the required quantity of ethyl ether of 2-cyanoacrylic acid at room temperature with the required quantities of butyl or hexyl ether of acrylic acid and 1,1-dioxotetrahydro-1$\lambda^6$-thiophene-3-ilic ether of 2-methacrylic acid and stir at room temperature until the complete dissolution of the components.

Disadvantages of the known medical glue are insufficient storage stability and unpleasant odor.

Known (SU Inventor's Certificate 1005455) is medical glue comprising ethyl-1-cyanoacrylate, 3-methacryloxysulpholane and butylacrylate. In said composition, ethyl-1-cyanoacrylate is the adhesive binder, 3-methacryloxysulpholane is the anti-inflammatory and antimicrobial component, and butylacrylate is the plasticizer. To produce said glue one should mix the required quantity of ethyl-1-cyanoacrylate with the required quantities of 3-methacryloxysulpholane and butylacrylate and stir at room temperature until the complete dissolution of the components. The composition was named Sulfacrylate.

The Sulphacrylate glue is used for gluing soft body tissues:
  in gastrointestinal tract surgery for sealing sutures and anastomoses and for the endoscopic stopping of gastrointestinal bleeding by glue sealing;
  in cardiovascular surgery for sealing heart sutures and vascular anastomoses;
  in liver and bile duel surgery for covering liver wound surfaces, sealing bile duet sutures and covering bile bed;
  during kidney, ureter and thyroid gland surgery;
  in respiratory apparatus surgery for additional bronchial stump strengthening after manual or mechanical broaching, covering lung parenchyma wounds (separately or with, pleural flap) and covering bronchial stump leaks and bronchial fistulas;
  in ophthalmology;

for gluing muscles and subcutaneous fat and covering skin wounds;

in plastic surgery of knee joint crucial ligaments for securing Lavsan tape in the bone canal;

as an additive for ultrasonic bonding of exfoliated intima with vessel wall and curing liver and skin wounds.

Disadvantages of the known medical glue are insufficient storage stability, unpleasant odor (the odor bouquet is formed when cyanoacrylate and butylacrylate are mixed) and high solidification rate of the adhesive film on the tissue.

The known medical glue is used as the closest counterpart of the present invention.

The technical objective achieved using the composition provided herein is to obtain medical glue with improved characteristics.

The technical result achieved by providing the medical glue having the composition provided herein is to increase the storage stability of the glue composition, improve the mechanical characteristics of the resultant glue film in medical applications, homogenize the solidification rate of the adhesive film on the tissue and improve the user characteristics (eliminate the sharp smell).

The medical glue having the composition provided herein comprises methacryloxysulpholane, N-butyl-2-cyanoacrylate and at least one stabilizer with the following component ratio (wt. %):

| Methacryloxysulpholane | 4.5-10.5 |
|---|---|
| Stabilizer | 0.2-1.1 |
| N-butyl-2-cyanoacrylate | balance. |

In a preferred embodiment of this invention, the medical glue comprises two stabilizers, i.e. an organic acid (formic, acetic, propionic or citric) and sulfur dioxide, wherein the organic acid content is 0.1 to 0.4 wt. %, and the sulfur dioxide content is 0.1 to 0.6 wt. %.

In the most preferred embodiment of this invention, the medical glue comprises (wt. %):

| Methacryloxysulpholane | 8.0-9.0 |
|---|---|
| Sulfur dioxide | 0.45-0.55 |
| Organic acid | 0.1-0.5 |
| N-butyl-2-cyanoacrylate | balance. |

To produce the medical glue having the composition provided herein, one should mix the required quantity of cooled N-butyl-2-cyanoacrylate with the required quantity of organic acid. Place the required quantity of methacryloxysulpholane into a container the inner surface of which was preliminarily treated with sulfur dioxide and pour in the earlier produced mixture of cooled N-butyl-2-cyanoacrylate and organic acid, permanently stirring the product until the complete dissolution of methacryloxysulpholane.

Methacryloxysulpholane acts as a anti-inflammatory and antimicrobial component in the composition.

N-butyl-2-cyanoacrylate acts as the adhesive binder in the composition.

The invention will be further disclosed using the following exemplified embodiments.

1. Mix 89.95 g cooled N-butyl-2-cyanoacrylate with 0.1 g ice-cold acetic acid. Place 8.5 g methacryloxysulpholane in a 0.5 dm$^3$ glass container the inner surface of which was preliminarily treated with 0.45 g sulfur dioxide pour in the earlier produced mixture of cooled N-butyl-2-cyanoacrylate and organic acid, permanently stirring the product until the complete dissolution of methacryloxysulpholane. The product medical glue film has the following parameters (compared with the Sulfacrylate glue as the closest counterpart):

1. Stability of properties (storage life) at least 1.5 times longer.
2. Bending strength 17-21% higher.
3. Relative elongation 13-17% higher.
4. Mechanical strength 15-17% higher,
5. Resolution in body in 30-40 days.
6. Tissue propagation through glue film 9-11% higher.
7. No smell.
8. More homogeneous solidification rate.

2. The glue is composed as per Example 1 but with 91.45 g N-butyl-2-cyanoacrylate. Film characteristics are as in Example 1.

3. The glue is composed as per Example 1 but with 9.0 g methacryloxysulpholane. Film characteristics are as in Example 1.

4. The glue is composed as per Example 1 but with 0.5 g citric acid. Film characteristics are as in Example 1.

5. The glue is composed as per Example 1 but with 91.45 g N-butyl-2-cyanoacrylate, 0.5 ice-cold acetic acid, 0.55 g sulfur dioxide and 9.0 g methacryloxysulpholane. Film characteristics are as in Example 1.

6. The glue is composed as per Example 1 but with 89.0 g N-butyl-2-cyanoacrylate. The bending strength, mechanical strength and relative elongation degrade, and the solidification rate becomes inhomogeneous.

7. The glue is composed as per Example 1 but with 92.0 g N-butyl-2-cyanoacrylate. The tissue propagation through the film degrades, and film resolution in body takes a significantly longer time.

8. The glue is composed as per Example 1 but with 7.5 g methacryloxysulpholane. Glue exposed tissue inflammation occurs.

9. The glue is composed as per Example 1 but with 9.5 g methacryloxysulpholane. The mechanical properties of the film degrade.

10. The glue is composed as per Example 1 but with 0.08 g food compatible organic acid. Glue stability degrades.

11. The glue is composed as per Example 1 but with 0.55 g food compatible organic acid. Glue solidification time degrades.

12. The glue is composed as per Example 1 but with 0.4 g sulfur dioxide. Glue stability degrades.

13. The glue is composed as per Example 1 but with 0.6 g sulfur dioxide. Glue exposed tissue inflammation occurs.

The resultant medical glue is used by analogy with the Sulfacrylate glue.

The glue can be used in cardiac surgery, pediatric cardiac surgery, vascular surgery, neurosurgery, ENT surgery, pediatric surgery, general surgery, thoracic surgery, gynecological surgery, gastrointestinal tract endoscopy, interventional radiology, cardiac neuroradiology and urological surgery.

The use of the medical glue having the composition provided herein increases the storage stability of glue composition characteristics, improves the mechanical characteristics of the resultant glue film in medical applications, homogenizes the solidification rate of the adhesive film on the tissue and improves the user characteristics (eliminates the sharp smell).

What is claimed is:

1. An odorless medical glue, comprising: cyanoacrylate ether and 3-methacryloxysulpholane, wherein said medical glue further comprises at least one stabilizer, and said cyanoacrylate ether is N-butyl-2-cyanoacrylate, the component ratio being as follows (wt. %):

| | |
|---|---|
| Methacryloxysulpholane | 4.5-10.5 |
| Stabilizer | 0.2-1.1 |
| N-butyl-2-cyanoacrylate | balance, | thus achieving a reduction of an unpleasant odor, wherein the stabilizer comprises sulfur dioxide in an amount of no less than 0.45 wt %-no more than 0.55 wt % based on the total wt % of the composition.

2. The medical glue of claim 1, wherein said medical glue comprises two stabilizers.

3. The medical glue of claim 2, wherein said stabilizers are organic acid and sulfur dioxide.

4. The medical glue of claim 1, wherein said medical glue comprises (wt. %):

| | |
|---|---|
| Methacryloxysulpholane | 8.0-9.0 |
| Sulfur dioxide | 0.45-0.55 |
| Organic acid | 0.1-0.5 |
| N-butyl-2-cyanoacrylate | balance. |

5. A method of producing odorless medical glue comprising mixing glue components, wherein a required quantity of methacryloxysulpholane is mixed with a mixture of a required quantities of cooled N-butyl-2-cyanoacrylate and stabilizer and stirred wherein the stabilizer comprises sulfur dioxide, said stabilizer is present in an amount no less than total 0.45 wt % and no more than total 0.55 wt % based on the total wt % of the composition.

6. The method of claim 5, wherein cooled N-butyl-2-cyanoacrylate is mixed with a required quantity of organic acid as a stabilizer.

7. The method of claim 5, wherein 3-methacryloxysulpholane is placed into a container, wherein the inner surface of the container for 3-methacryloxysulpholane is preliminarily treated with sulfur dioxide as a stabilizer wherein the stabilizer comprises sulfur dioxide, said stabilizer is present in an amount no less than total 0.45 wt % and no more than total 0.55 wt % based on the total wt % of the composition.

* * * * *